United States Patent [19]

Hansen

[11] 4,124,638

[45] Nov. 7, 1978

[54] SOLUBILIZABLE POLYACRYLAMIDE GELS CONTAINING DISULFIDE CROSS-LINKAGES

[76] Inventor: John N. Hansen, 9794 Cottrell Ter., Silver Spring, Md. 20903

[21] Appl. No.: 832,385

[22] Filed: Sep. 12, 1977

[51] Int. Cl.$^2$ .......................................... C07C 103/153
[52] U.S. Cl. ................................................. 260/561 S
[58] Field of Search ..................................... 260/561 S

[56] References Cited

U.S. PATENT DOCUMENTS

| | | | |
|---|---|---|---|
| 2,625,565 | 1/1953 | Snell et al. ......................... | 260/561 S |
| 2,701,256 | 2/1955 | Kuhn et al. ..................... | 260/561 S X |
| 3,313,850 | 4/1967 | Bahr et al. ......................... | 260/561 S |
| 3,352,898 | 11/1967 | James ............................. | 260/561 S X |
| 3,365,480 | 1/1968 | Cobb et al. ..................... | 260/561 S X |
| 3,914,301 | 10/1975 | Miller et al. ....................... | 260/561 S |

*Primary Examiner*—Allen B. Curtis

[57] ABSTRACT

Solubilizable polyacrylamide gels are made by polymerizing acrylamide in the presence of a cross-linking agent which contains a disulfide bridge. The resulting gel is soluble in the presence of reducing agents which convert the disulfide bridge into the corresponding free sulfydryl form.

1 Claim, No Drawings

SOLUBILIZABLE POLYACRYLAMIDE GELS CONTAINING DISULFIDE CROSS-LINKAGES

SUMMARY OF THE INVENTION

It is the object of this invention to prepare a novel polyacrylamide gel which is easily solubilized under conditions which are harmless to a wide range of biological substances. It is apparent to those skilled in the use of polyacrylamide gels that this provides a route for the convenient recovery of substances from the gels.

Polyacrylamide gels are frequently used for the separation of biological molecules (e.g., nucleic acids, proteins, etc.), but have been limited because sample recovery has been difficult. Although some kinds of polyacrylamide gels can be solubilized, the chemistry of cross-linkages used heretofore precludes the use of mild solubilizing conditions. This invention provides a new class of cross-linkage which contains a disulfide bridge. Since disulfide bridges can be broken under biologically mild reducing conditions, acrylamide gels containing this type of cross-linkage are easily dissolved. The description of this invention includes the synthesis of a new compound with the structure ($CH_2$=$CHCONHCH_2CH_2S$—$)_2$ which contains a suitable disulfide bridge, as well as the formation and solubilization of disulfide cross-linked gels, and recovery of nucleic acids from the solubilized gel.

DESCRIPTION OF THE INVENTION

A disulfide-containing cross-link can be synthesized as follows. Dissolve a 4-gram amount of cystamine dihydrochloride in 40 ml of 3.12 M NaOH. Combine with 40 ml of chloroform containing 4.3 ml of acrylylcloride. Stir for 15 min while maintaining the temperature near 50° C. Discard the aqueous phase, cool the organic phase, and recover the product by filtration. Recrystallize twice from chloroform. The infrared spectrum (KBr pellet) has major peaks at 3260, 3070, 1650 (shoulder), 1610, 1510, 1310, 1250, 1230, 1070, 985, 960, and 805 $cm^{-1}$. The nmr spectrum ($CDCl_3$, TMS) gives $\delta$ = 2.92(2H) triplet, 3.72(2H) quartet, 5173(1H) multiplet, 6.32(2H) multiplet, and 6.77(1H) broad. The elemental analysis of the compound gives: C, 45.70; H, 6.37; N, 10.74; S, 24.87. The data establish the structure as ($CH_2$=$CHCONHCH_2CH_2S$—$)_2$. The mp is 121°–123° C. A trivial name for this compound is bis-acrylylcystamine.

A solubilizable gel can be formed using acrylamide and this disulfide compound as a cross-linking agent in a free-radical reaction. The best method for preparing these gels is in an ammonium persulfate-initiated reaction, using tetremethylethylenediamine (TEMED) as a catalyst, and a tris-borate buffer. In all gels, the acrylamide:bis-acrylylcystamine ratio is 12:1 by weight. The "gel %" refers to the concentration of total monomers, in % by weight. The tris-borate buffer consists of 10.8 g tris(hydroxymethyl)aminomethane, 5.5 g of boric acid, and 0.93 g of disodium EDTA per liter of water, pH 8.3. The "gel %" can be varied over a wide range. The conditions for forming the gel are as follows:

| % gel | 3.5 | 5.0 | 7.5 | 10.0 | 12.5 |
|---|---|---|---|---|---|
| % TEMED | 0.08 | 0.25 | 2.0 | 5.6 | 6.1 |
| % persulfate | 0.12 | 0.12 | 0.02 | 0.08 | 0.06 |

The gels are polymerized in the presence of tris-borate buffer for 40 min at 40° C. in "Plexiglas" tubes, 4 mm I.D. × 10 cm long, sealed over the bottom with plastic film. Excess TEMED can be removed by electrophoresis. This is important for gels containing more than 0.5% TEMED, because it changes the pH and conductivity of the gel. The electrophoresis is carried out in a common disc-gel device, using tris-borate buffer in both the upper and lower chambers. Electrophoresis for 12 hours at 100 V removes the TEMED completely.

These gels are all readily solubilized by sulfhydryl-containing reducing agents. All sulfhydryl compounds which have been tested are effective. These include 2-mercaptoethanol, dithiothreitol, dithioerythritol, cysteine, and butanethiol. For reasons of economy and convenience, mercaptoethanol is generally preferred. The gels can be solubilized by adding 0.1 ml of mercaptoethanol per gram of gel. After 30 min, addition of 10 volumes of water yields a simple solution.

This novel gel allows the easy recovery of substances which are in the gel. In practice of one embodiment of this invention, the recovery or ribonucleic acid (RNA) is carried out. A 25 microgram amount of ribosomal RNA is applied to the top of a 3.5% gel prepared as above. Electrophoresis is carried out at 100 V for an hour, or until the separation is complete. The gels can be stained with 0.001% toluidine blue 0 in 1% acetic acid to visualize the bands, or alternatively, the gels can be scanned in a gel scanner at 260 nm to locate desired bands. Once the position of the RNA has been ascertained, the portion of the gel containing the RNA can be excised with a razor blade. The piece of gel is weighed, and one-tenth volume (by weight) of mercaptoethanol is added. After occasional stirring for several minutes (10 min is usually sufficient), 10 volumes of water are added. The RNA is then recovered from the solution by application to 2.5 ml of hydroxyapatite in a 5 ml syringe which had been washed with 0.01 M SPB (SPB is an equimolar solution of mono- and dibasic forms of sodium phosphate). The gel components are completely washed off with additional 0.01 M SPB. This is followed by a wash of 0.12 M SPB to remove traces of other contaminants. The RNA is then recovered by washing the column with 0.4 SPB. Final yield of RNA is in the range of 50–60%.

Although this invention has been developed using RNA as the biological material to be separated on the gel and subsequently recovered after solubilization of the gel, it is obvious to those skilled in the art that this procedure is directly applicable to all procedures which have employed the old type (i.e., non-solubilizable) of polyacrylamide gels. These procedures therefore fall within the scope of the invention.

It is also obvious that a wide range of disulfide-containing cross-linkages (i.e., other than bis-acrylylcystamine) could be designed for use in other gel formulations, and also fall withing the scope of this invention.

What is claimed is:

1. A composition of matter having the structure:

$CH_2$=$CHCONHCH_2CH_2SSCH_2CH_2N$-$HOCCH$=$CH_2$

* * * * *